United States Patent
Miyawaki (10) Patent No.: US 6,443,884 B1
(45) Date of Patent: Sep. 3, 2002

(54) VENTRICULAR ASSIST DEVICE CAPABLE OF PROMOTING RECOVERY OF CARDIAC FUNCTION

(76) Inventor: Fujio Miyawaki, Aimufujimino-minami-ichibankan #602, 3369, Katsuse, Fujimi-shi, Saitama (JP)

( * ) Notice: Subject to any disclaimer, the term of this patent is extended or adjusted under 35 U.S.C. 154(b) by 0 days.

(21) Appl. No.: 09/647,860
(22) PCT Filed: Apr. 5, 1999
(86) PCT No.: PCT/JP99/01785
§ 371 (c)(1),
(2), (4) Date: Oct. 6, 2000
(87) PCT Pub. No.: WO99/51285
PCT Pub. Date: Oct. 14, 1999

(30) Foreign Application Priority Data

Apr. 6, 1998 (JP) .................... 10-093392 (P)

(51) Int. Cl.⁷ .............................. A61N 1/362
(52) U.S. Cl. ........................ 600/17; 623/3.28
(58) Field of Search ............... 600/16–18; 604/4.01, 604/6.1, 6.11, 6.14; 623/3.1, 3.28

(56) References Cited

U.S. PATENT DOCUMENTS

| | | | |
|---|---|---|---|
| 4,782,817 A | 11/1988 | Singh et al. | |
| 5,437,601 A | 8/1995 | Runge | |
| 6,039,078 A | * 3/2000 | Tamari | |

FOREIGN PATENT DOCUMENTS

| | | |
|---|---|---|
| JP | 55-141250 | 11/1980 |
| JP | 58-169463 | 10/1983 |
| JP | 63-66220 | 12/1988 |
| JP | 6-11310 | 2/1994 |

OTHER PUBLICATIONS

European Search Report.

* cited by examiner

Primary Examiner—Mark Bockelman
(74) Attorney, Agent, or Firm—McDermott, Will & Emery (57) ABSTRACT

A ventricular assist device 10 includes a blood conduit 14, which carries the blood ejected from the ventricle to the ventricular assist device, a one-way valve 22, which is provided in the blood conduit and can open only toward the ventricular assist device, an afterload-controlling chamber 11, which temporarily stores the blood ejected from the ventricle, a pressure sensor 23, which measures the pressure in the afterload-controlling chamber, a blood pump 25 and a control unit 26 thereof, a blood conduit 16 that carries the blood to an artery, and a probe 27 for measuring blood flow rate and a flowmeter 28, which control the flow rate of the blood pump 25. The pressure of the afterload-controlling chamber 11 is controlled so as to keep the one-way valve closed during ventricular diastole, and also controlled so as to direct all the blood ejected from the ventricle into the afterload-controlling chamber 11 during ventricular systole. Therefore, a new ventricular assist device can be provided, which enables the native heart to eject blood with very low ejection resistance and ensures sufficient ventricular relaxation and filling.

19 Claims, 6 Drawing Sheets

VENTRICULAR ASSIST DEVICE CAPABLE OF PROMOTING RECOVERY OF CARDIAC FUNCTION

TECHNICAL FIELD

The present invention relates to a ventricular assist device used for circulatory assistance of a patient suffering from heart failure, methods of controlling the same, and an auxiliary apparatus therefor. More particularly, the present invention relates to a ventricular assist device capable of promoting recovery of the function of the native failing heart, methods of controlling the same, and an auxiliary apparatus therefor.

BACKGROUND ART

Figure 11:
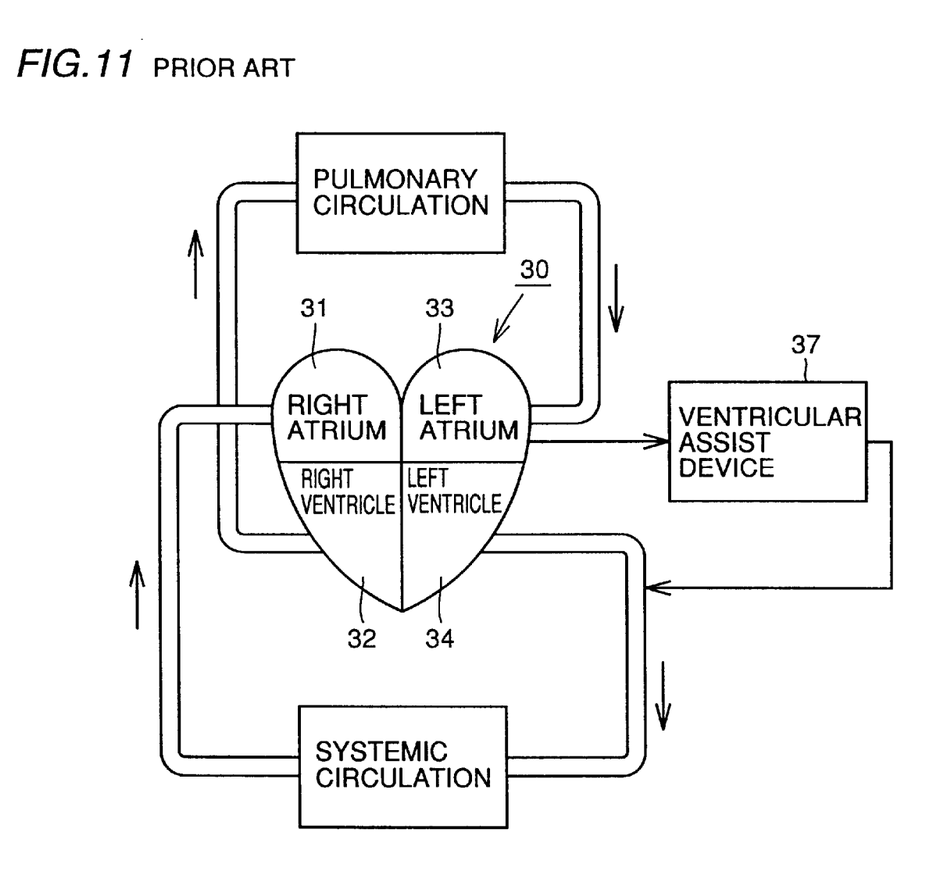
FIG. 11 shows a manner of attachment of a conventional ventricular assist device to a native heart.

A ventricular assist device for circulatory assistance, as an example of a ventricular assist device of interest to the present invention, is disclosed in Japanese Patent Laid-Open No. 55-141250. FIG. 11 shows a manner of attachment of the ventricular assist device to the native heart. As shown in FIG. 11, the human heart 30 is composed broadly of the right heart for the pulmonary circulation and the left heart for the systemic circulation. The right heart is divided into the right atrium 31 and the right ventricle 32; the left heart, into the left atrium 33 and left ventricle 34. The blood flows in the following order: the venous blood returning from the systemic circulation enters the right atrium through the superior and inferior venae cavae, and then passes into the right ventricle, whose contraction forces it through pulmonary artery to the lung. There, it is oxygenated by the function of respiration, and next is returned through the pulmonary veins to the left atrium 33. After this, the blood enters the left ventricle 34 and is pumped into the aorta by the contraction of left ventricle 34, and then back to the systemic circulation. Here, a ventricular assist device 37 is used to pump blood from the left atrium 33 or left ventricle 34 into the aorta.

Conventional ventricular assist devices have been used in the above-described manner. The conventional ventricular assist device is in an operational mode such that it sucks blood from the native heart 30 and the ventricular assist device 37 pumps the blood into the artery. This operational mode suggests that the conventional ventricular assist device is mainly designed to functionally substitute for an incompetent native heart 30.

Therefore, the higher the flow rate of the conventional ventricular assist device, the smaller the amount of blood loaded in the ventricle during diastole, thus impairing relaxation and filling of the native heart 30. Furthermore, in most cases, the native heart 30 has to eject some amount of blood into the aorta against the aortic pressure, although the ventricular assist device draws sufficient blood, suggesting that the ejection resistance is too high for the heart with insufficient function. To summarize, the conventional ventricular assist device does not provide the ideal environment for recovery of the function of native heart 30, because it impairs relaxation and filling of native heart 30 and imposes high ventricular load.

Therefore, an object of the present invention is to provide a ventricular assist device capable of promoting recovery of an incompetent native heart.

Another object of the present invention is to provide a ventricular assist device, which is not only capable of promoting the recovery of a failing heart but also available in the case of ineffective contraction of the heart, as seen in ventricular fibrillation.

The other object of the present invention is to provide an auxiliary apparatus, which is capable of promoting the recovery of a failing native heart, for a conventional ventricular assist device.

DISCLOSURE OF THE INVENTION

A ventricular assist device in accordance with the present invention includes a blood conduit that carries blood from the ventricle toward the ventricular assist device, a one-way valve that is provided within the blood conduit and can open only toward the ventricular assist device, an afterload-controlling chamber that temporarily stores the blood ejected through the one-way valve from the ventricle of native heart, pressure-controlling means for maintaining pressure of the afterload-controlling chamber within such a predetermined range that is lower than the arterial pressure and higher than the ventricular diastolic pressure, a blood pump that draws blood from the afterload-controlling chamber and pumps the blood into the artery, a control unit for the blood pump, and a feeding tube.

During ventricular diastole, the pressure of afterload-controlling chamber is maintained at pressure levels that can close the one-way valve, which opens only toward the afterload-controlling chamber. Thereby, the blood pump does not suck the blood from the ventricle, and neither relaxation of the ventricle nor filling is limited. During ventricular systole, the pressure of afterload-controlling chamber is maintained sufficiently lower than the arterial pressure. Therefore, the ventricle is able to eject blood into the afterload-controlling chamber with very low ejection resistance, but not into the artery with much higher ejection resistance. The blood ejected into the afterload-controlling chamber is sucked and fed to the artery by the blood pump that is provided distal to the afterload-controlling chamber. As a result, the ventricle is able to eject blood with a low ejection resistance after sufficient relaxation and filling of the ventricle. Therefore, the functional recovery of native failing heart can be promoted.

BEST MODE FOR CARRYING OUT THE INVENTION (1) First Embodiment

Figure 1:
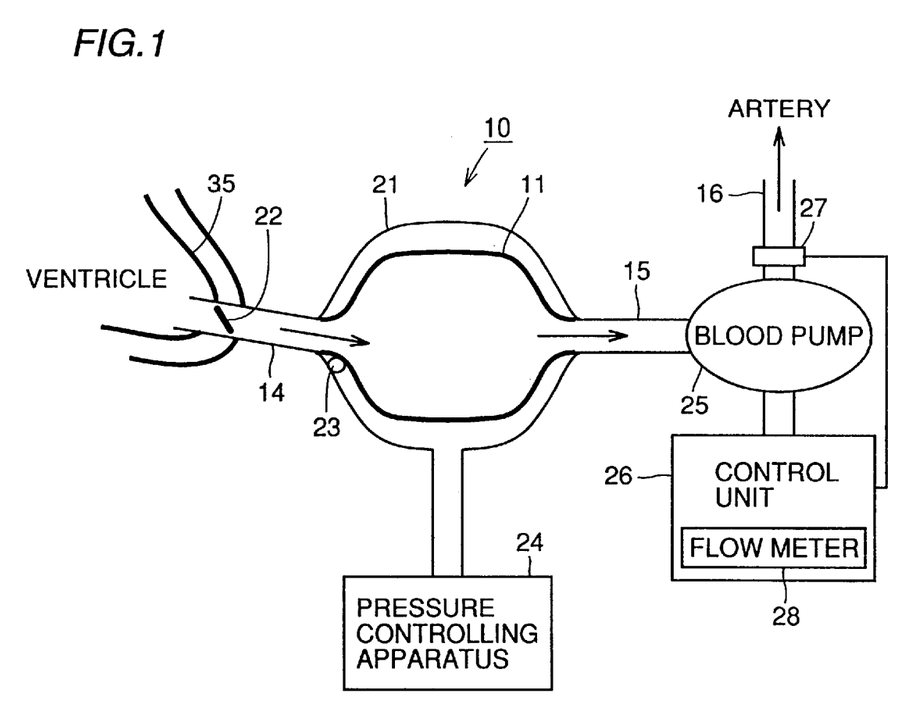
FIG. 1 is a schematic diagram demonstrating a configuration of a ventricular assist device in accordance with the first embodiment.

Referring to the drawings, an embodiment of the present invention will be described as follows. FIG. 1 shows a schematic diagram illustrating a ventricular assist device 10 in accordance with the first embodiment of the present invention implanted in a ventricle 35 (left ventricle 34 or right ventricle 32) of a native heart 30. As shown in FIG. 1, the ventricular assist device 10 includes the following components: a one-way valve 22 that can open only toward an afterload-controlling chamber 11; a blood conduit 14 containing the one-way valve; an afterload-controlling chamber 11 that temporarily stores the blood ejected through the one-way valve 22 by the contraction of ventricle 35; a pressure sensor 23 of the afterload-controlling chamber 11; a blood conduit 15 provided distal to the afterload-controlling chamber 11; a blood pump 25 connected thereto; a control unit 26 for driving and controlling the blood pump 25; a blood conduit 16 for carrying blood to the artery; a flow probe 27; and a flowmeter 28 connected thereto. The flowmeter is contained within or linked to the control unit 26. By means of a housing 21, which covers the afterload-controlling chamber 11 entirely, and a pressure-controlling apparatus 24, which is connected thereto, the pressure in the afterload-controlling chamber 11 is controlled so as to be sufficiently lower than the arterial pressure during the systole of ventricle 35, and is maintained at pressure levels that can keep the one-way valve 22 closed during the diastole of ventricle 35. As a result, during the diastole of ventricle 35, the blood of ventricle 35 is not sucked by the blood pump 25 because the one-way valve 22 is kept closed, therefore allowing the sufficient relaxation and filling of the ventricle 35. During systole, the ventricle 35 can eject blood into the afterload-controlling chamber 11 with a low ejection resistance. The blood pump 25 provided distal to the afterload-controlling chamber 11 under the control of the control unit 26 draws blood from the afterload-controlling chamber 11, and pumps into the artery. The pressure-controlling apparatus 24 is, for example, an air-driven pump. By adjusting the pressure of air in the space between the afterload-controlling chamber 11 and the housing 21, the pressure in the afterload-controlling chamber 11 is kept within the above-described range. The pressure of afterload-controlling chamber may also be controlled, as will be described later, by adjusting the flow rate of the blood pump 25 under the control of the control unit 26.

The ventricle 35 and the afterload-controlling chamber 11 are connected with a blood conduit 14 in between. The blood conduit 14 may be an anti-thrombogenic cannula provided with a one-way valve 22, an artificial blood vessel with a one-way valve 22, or an arterial homo- or xenograft with a one-way valve 22. The blood pump 25 and afterload-controlling chamber 11 are connected with a blood conduit 15 in between. The blood conduit 15 may be an anti-thrombogenic cannula, or an artificial blood vessel. The blood conduit 16 for carrying blood to the artery may be an anti-thrombogenic cannula, or an artificial blood vessel.

Figure 7:
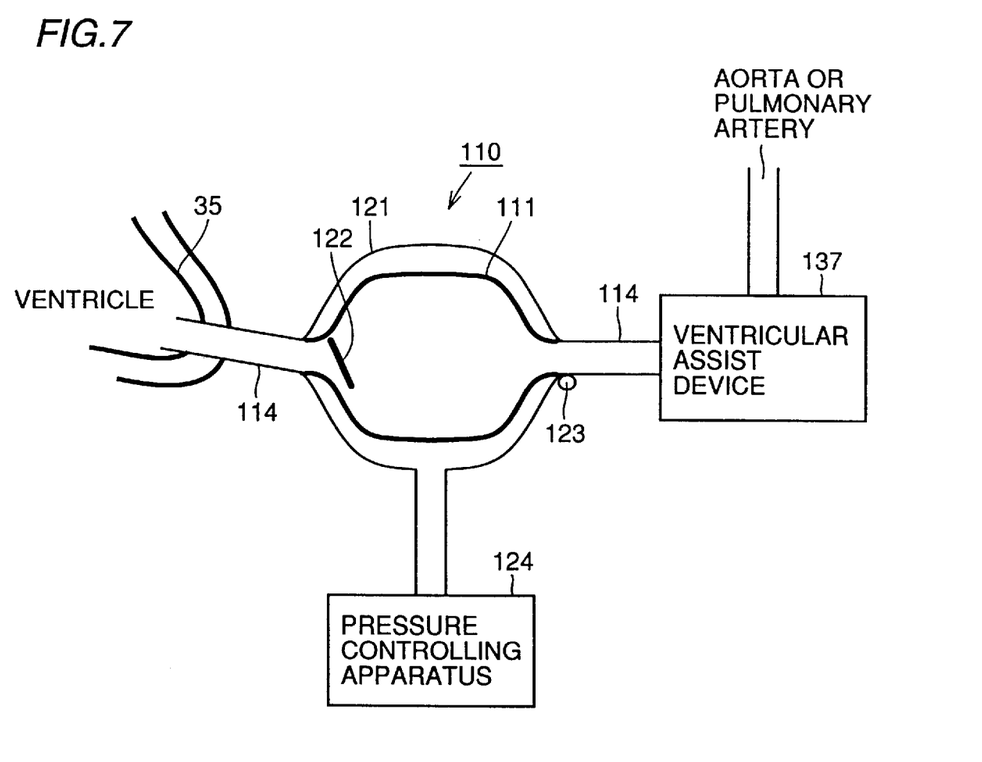
FIG. 7 is a schematic diagram demonstrating a configuration of an auxiliary apparatus for a ventricular assist device in accordance with the third embodiment of the present invention.

The one-way valve 22 may be a mechanical valve with one or two tilting discs, or may be a biological valve prepared by processing homogeneic or xenogeneic tissues such as a cardiac valve or a pericardium. The one-way valve 22 is fixed within or integrally formed within the blood conduit 14. The one-way valve 22 may be provided at any position along the blood conduit 14. The one-way valve may be positioned at an inflow portion of the afterload-controlling chamber 11, as shown in FIG. 7.

Figure 2:
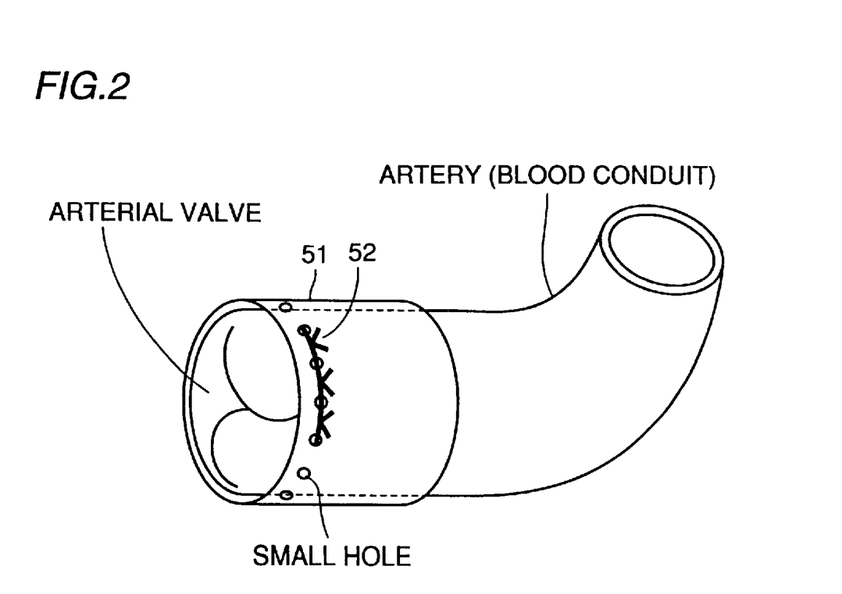
FIG. 2 indicates an example of integration of a one-way valve and a blood conduit, or a valved conduit, which is made of a homogeneic or xenogeneic great artery with a valve.

As an example of the integration of both the one-way valve 22 and blood conduit 14, a homo- or xenogeneic ascending aorta with the aortic valve or a homo- or xenogeneic pulmonary artery with the pulmonary valve may be used. In this case, the root portion of the aorta or the pulmonary artery, namely, the segment extending from the valvular annulus to a portion where the aorta or the pulmonary artery penetrates the wall of the ventricle 35, is reinforced with a ring made of firm material. FIG. 2 shows this example. The reinforcing ring 51 and the aorta or the pulmonary artery may be fixed together by sewing the valvular annulus and the reinforcing ring 51 together with a suture 52. In order to facilitate this fixation with the suture, the reinforcing ring 51 may be provided with a number of small holes, through which the suture 52 is passed. The material of reinforcing ring 51 is, for example, a titanium alloy, firm plastics or others. FIG. 2 demonstrates that a great artery with a valve is partially sewn to the reinforcing ring 51 with the suture 52.

Figure 3:
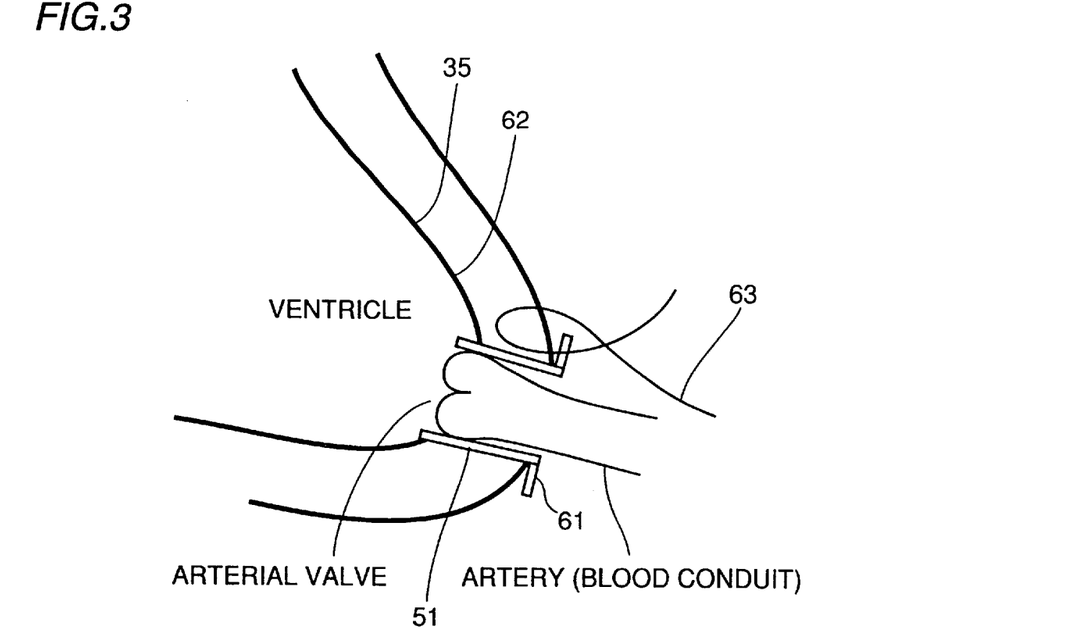
FIG. 3 shows an example in which the valved conduit utilizing the homogeneic or xenogeneic great artery with a valve is inserted into the ventricle.

In all the aforementioned various blood conduits 14, a portion penetrating through the wall of the ventricle 35 may be covered with a cloth (for example, made of polyethylene glycol terephthalate) with a flange 61. The flange 61 and ventricular wall 62 are sewn together with a suture 63 so as to prevent bleeding from the site where the blood conduit 14 is inserted into the ventricle 35. This also serves to prevent slipping out of the blood conduit 14. FIG. 3 shows that the blood conduit 14 is fixed in the ventricular wall 62 by suturing together the flange 61, which is attached to the reinforcing ring 51, and the ventricular wall 62 with a suture 63.

The blood pump 25 connected distal to the afterload-controlling chamber 11 may be a pulsatile blood pump (diaphragm type, sack type, pusher plate type, or others) with inflow and outflow valves, or it may be a non-pulsatile blood pump (centrifugal pump, roller pump, or others) without any inflow or outflow valve.

The portion that stores the ejected blood in the afterload-controlling chamber 11 may be made from a flexible anti-thrombogenic material, for example, solely from a synthetic material such as polyurethane, segmented polyurethane or others. It may be also made from a flexible material (silicone rubber, polyurethane or others) with its surface processed with a biological substance such as heparin or others.

Figure 4:
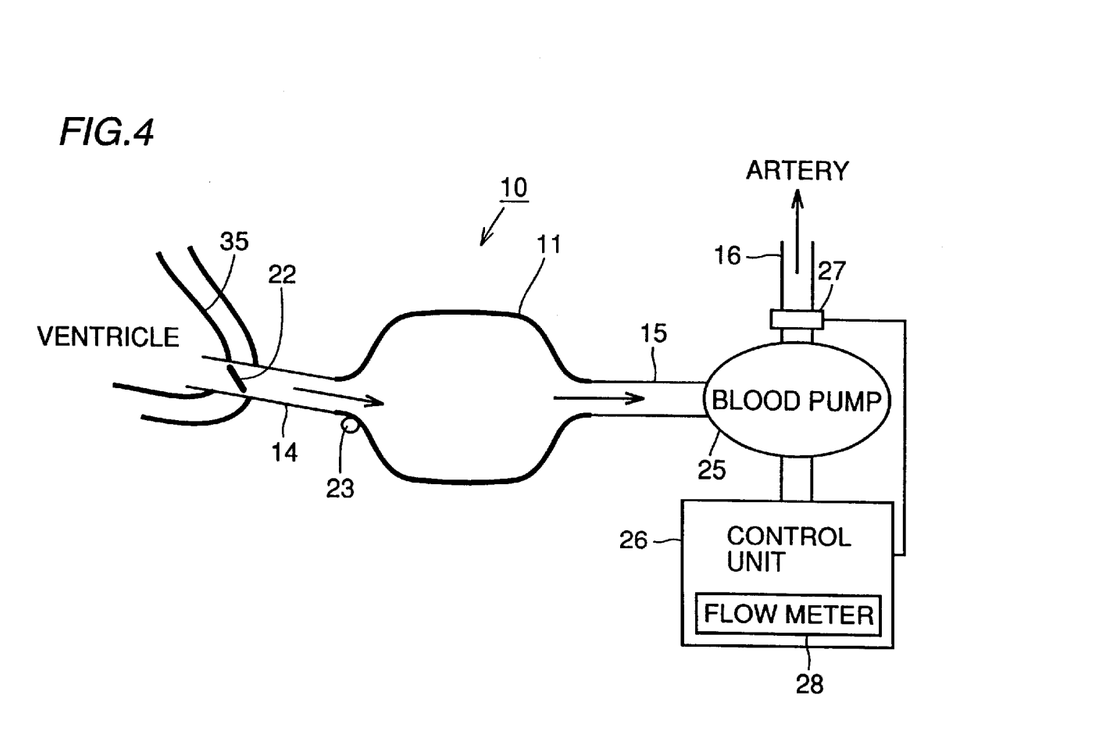
FIG. 4 indicates a simplified variation of the first embodiment shown in FIG. 1.

FIG. 4 shows a simplified variation of the ventricular assist device 10 shown in FIG. 1. In this example, the afterload-controlling chamber 11 is not covered with the housing 21, and the pressure-controlling apparatus 24 is not provided, either.

The method of controlling the pressure of afterload-controlling chamber 11 in the ventricular assist device 10 shown in FIGS. 1 and 4 will be described as follows.

1) First, as already described, a pressure sensor 23 is provided for the afterload-controlling chamber 11. By monitoring the pressure measured with the pressure sensor 23, the flow rate of blood pump 25 is adjusted with the control unit 26 so that the pressure of afterload-controlling chamber 11 is kept within the above-described predetermined range. More specifically, when the pressure exceeds the predetermined range, the flow rate of blood pump 25 is increased, and when the pressure is lower than the lower limit, the flow rate is reduced. The measurement of blood flow necessary for the flow rate control is achieved with a flow probe 27, which is attached to a blood conduit 16, and a flowmeter 28 (electromagnetic flowmeter, ultrasonic flowmeter, or others) connected to the probe 27. The flowmeter is contained in or linked to the control unit 26. The flow probe 27 for flow measurement may also be attached to the blood conduit 15. This method of pressure control in the afterload-controlling chamber 11 is employed in the simplified variation shown in FIG. 4.

2) When the blood pump 25 is pulsatile, a function of synchronizing the contraction of ventricle 35 with the blood suction from the afterload-controlling chamber 11 is provided additionally (specifically by utilizing the electrocardiography). This prevents increasing blood volume by the inflow of blood from ventricle 35, and thereby prevents an increase in pressure of afterload-controlling chamber 11.

3) When the afterload-controlling chamber 11 is provided with the housing 21 as shown in FIG. 1, a finer pressure control of afterload-controlling chamber 11 is possible by further controlling the pressure in the housing 21. When the blood pump 25 is non-pulsatile, it may be preferable to provide the afterload-controlling chamber 11 with the housing 21 because the finer pressure control of afterload-controlling chamber 11 is possible.

Using one or more of the above-described methods, the pressure of afterload-controlling chamber 11 is controlled.

Next, the shape of afterload-controlling chamber 11 will be described. When the housing 21 is provided, the shape of the afterload-controlling chamber 11 other than the housing 21 is designed, for example, by the hydrodynamic finite element method so as to prevent as much separation and disturbance of blood stream as possible.

The volume of the portion storing the ejected blood in the afterload-controlling chamber 11 ranges from approximately 10 to approximately 1000 cc.

The pressure in the afterload-controlling chamber 11 may be set higher than ventricular diastolic pressure, during diastole so that the one-way valve 22 is kept closed, and may be set lower than the arterial pressure during systole (the aortic pressure when assisting the left heart, and the pulmonary artery pressure when assisting the right heart). It should be noted that when the native heart is weaned from the blood pump 25, the pressure of afterload-controlling chamber 11 during systole is gradually increased and finally set to be equal to or higher than the arterial pressure (the aortic pressure when assisting the left heart, and the pulmonary artery pressure when assisting the right heart), so that the blood in the ventricle is directly ejected into the artery, but not into the blood pump 25.

(2) Second Embodiment

Figure 5:
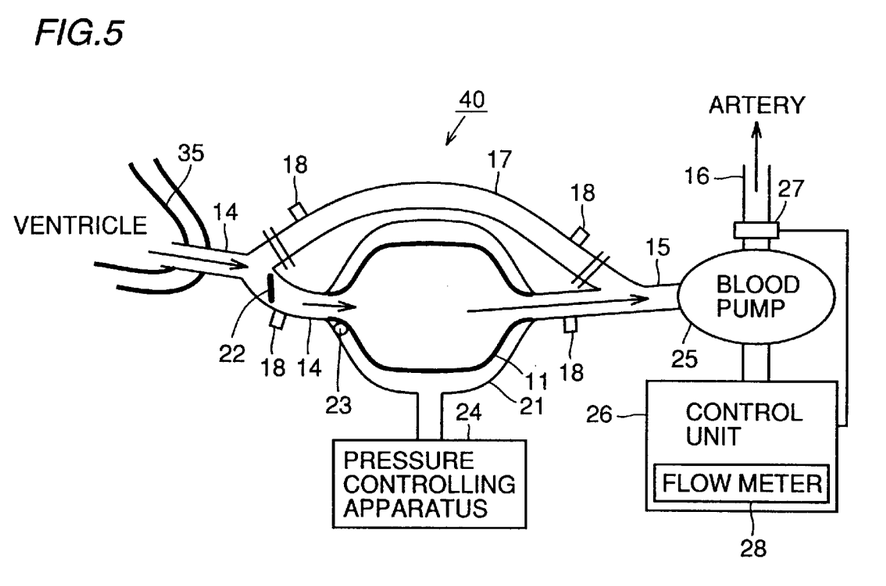
FIG. 5 represents the second embodiment of the present invention.
Figure 6:
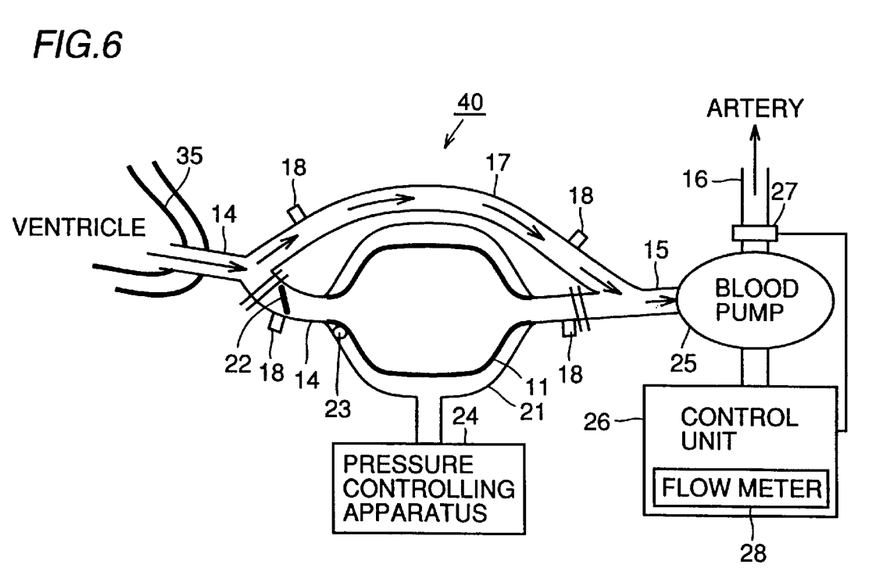
FIG. 6 represents the second embodiment of the present invention.

The second embodiment of the present invention will be described as follows. This embodiment enables the use of the ventricular assist device of the present invention even when effective contraction of heart is not obtained, for example, in the case of ventricular fibrillation. The embodiment is applicable both to the afterload-controlling chamber 11 with the housing 21 shown in FIG. 1 and to the simplified variation shown in FIG. 4. Based on the example shown in FIG. 1, a particular example of this embodiment is illustrated in FIGS. 5 and 6. FIGS. 5 and 6 show a particular example of a ventricular assist device 40 in accordance with the second embodiment. As shown in FIGS. 5 and 6, in the second embodiment, a bypass conduit 17 is provided parallel to the afterload-controlling chamber 11 of the first embodiment. Except for this portion, the configuration of the second embodiment is basically the same as that of the first embodiment. The bypass conduit 17 is made from the same anti-thrombogenic material as the blood conduit 15 of the ventricular assist device 10 in accordance with the first embodiment. When effective cardiac contractions are observed, the bypass conduit 17 is closed, and a route through the afterload-controlling chamber 11 is opened (FIG. 5). In this case, the second embodiment is functionally equivalent to the ventricular assist device 10 in accordance with the first embodiment.

When no effective cardiac contraction is observed, the route through the afterload-controlling chamber 11 is closed and the bypass conduit 17 is opened (FIG. 6). In this case, the second embodiment is functionally equivalent to a conventional ventricular assist device 37. In other words, like a conventional ventricular assist device 37, the blood in the ventricle 35 is sucked by the blood pump 25 and fed to the aorta (when assisting the left heart) or to the pulmonary artery (when assisting the right heart).

Ports 18 provided at two positions along each of the routes through the afterload-controlling chamber 11 and the bypass conduit 17, as shown in FIG. 5, are used when a medicine such as an anti-coagulant is needed. For example, heparin or others is administered through the port or ports 18 in order to prevent coagulation of the blood left within the route when the route is closed. Alternatively, the blood left in the route may be removed and the route is refilled with heparinized saline solution or others through the port or ports.

Although the pressure-controlling apparatus and the control unit for blood pump are described as separate components in the first and second embodiments, it goes without saying that the description is not limiting and these apparatuses may be integrated. This integration can provide a ventricular assist device reduced in size.

(3) Third Embodiment

Referring to the drawings, the third embodiment of the present invention will be described as follows. In the third embodiment, a part of the ventricular assist device of the first embodiment is provided as an auxiliary apparatus for a ventricular assist device between the native heart 30 and the existing ventricular assist device.

FIG. 7 is a schematic diagram demonstrating the auxiliary apparatus 110 in accordance with the present invention provided between the ventricle 35 Deft ventricle 34 or right ventricle 32) of native heart 30 and a ventricular assist device 137. As shown in FIG. 7, the auxiliary apparatus 110 for the ventricular assist device includes an afterload-controlling chamber 111 that temporarily stores the blood ejected from the ventricle 35, a one-way valve 122 that is provided at an inflow portion of the afterload-controlling chamber 111, and a pressure sensor 123 provided at an outflow portion of the afterload-controlling chamber 111. The one-way valve 122 can open only toward the afterload-controlling chamber 111. The one-way valve 122 may be positioned within a blood conduit 114, as shown in FIG. 1.

In general, a ventricular assist device 137 has a flowmeter that is linked with the ventricular assist device 137. Using a housing 121 that entirely covers the afterload-controlling chamber 111 and a pressure-controlling apparatus 124 that is connected with the housing, the pressure of afterload-controlling chamber 111 is kept within a predetermined range that is much lower than the arterial pressure during systole of ventricle 35, and is also maintained within a predetermined range that ensures closure of the one-way valve 122 during diastole of ventricle 35. Consequently, during the diastole of ventricle 35, the closure of the one-way valve 122 ensures sufficient relaxation and filling of ventricle 35 because the ventricular assist device 137 does not suck the ventricle 35. During systole, the ventricle 35 is able to eject blood with low ejection resistance into the afterload-controlling chamber 111. The blood in afterload-controlling chamber 111 is sucked and fed to the aorta by the ventricular assist device 137 provided distal to the afterload-controlling chamber 111. Irrespective of the presence/absence of the flowmeter in the ventricular assist device 137, the auxiliary apparatus 110 for the ventricular assist device may be provided with a flowmeter.

The pressure-controlling apparatus 124 may be an air-driven pump. The pressure in afterload-controlling chamber 111 is kept within the above-described range by adjusting the pressure of air in the space between the afterload-controlling chamber 111 and housing 121. The pressure control of the afterload-controlling chamber 111 may be also performed in combination with the adjustment of flow rate of ventricular assist device 137, as described later.

The ventricle 35, afterload-controlling chamber 111 and ventricular assist device 137 are connected with blood conduits 114. The blood conduit 114 is a cannula, an artificial blood vessel, or a homogeneic or xenogenic arterial tissue.

The one-way valve 122 is basically the same as that of the first embodiment. Therefore, as shown in FIG. 2, a valved conduit, in which a one-way valve 122 and a blood conduit 114 are integrated, may be used.

The blood pump of ventricular assist device 137 connected distal to the afterload-controlling chamber 111 may be a pulsatile pump (diaphragm type, sack type, or pusher-plate type) with inflow and outflow valves, or a non-pulsatile pump (centrifugal pump, roller pump, or others) without any inflow or outflow valve.

The portion that temporarily stores the ejected blood in the afterload-controlling chamber 111 may be made from a flexible anti-thrombogenic material, for example, solely from a synthetic material such as polyurethane, segment polyurethane, or others. It may be also made from a flexible material (vinyl chloride, polyurethane, or others) with its surface processed with a biological substance such as heparin or others.

Figure 8:
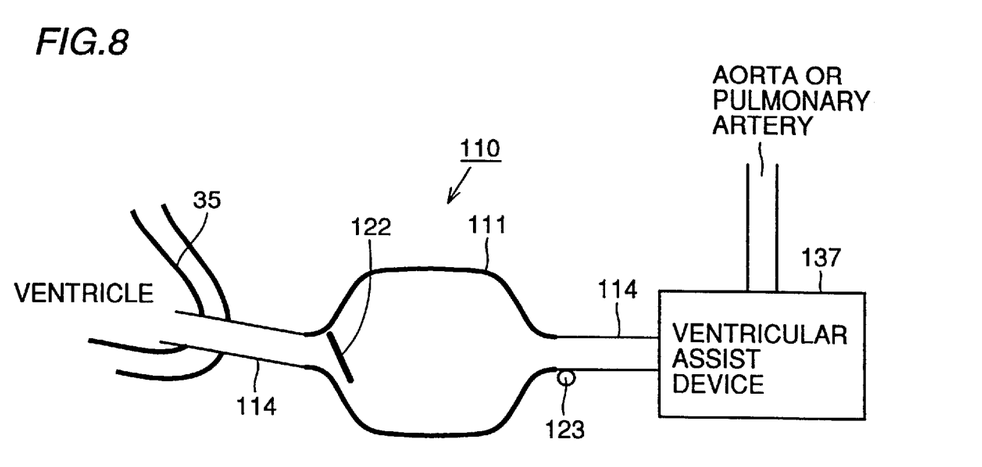
FIG. 8 indicates a simplified variation of the third embodiment shown in FIG. 7.

FIG. 8 demonstrates a simplified variation of the auxiliary apparatus 110, shown in FIG. 7, for a ventricular assist device. In this example, an afterload-controlling chamber 111 is not covered with a housing 121, and a pressure-controlling apparatus 124 is not provided either.

The method of controlling the pressure of afterload-controlling chamber 111 in the auxiliary apparatus 110, shown in FIGS. 7 and 8, for the ventricular assist device is the same as that in the first embodiment. Therefore, its description is not repeated again.

(4) Fourth Embodiment

Figure 9:
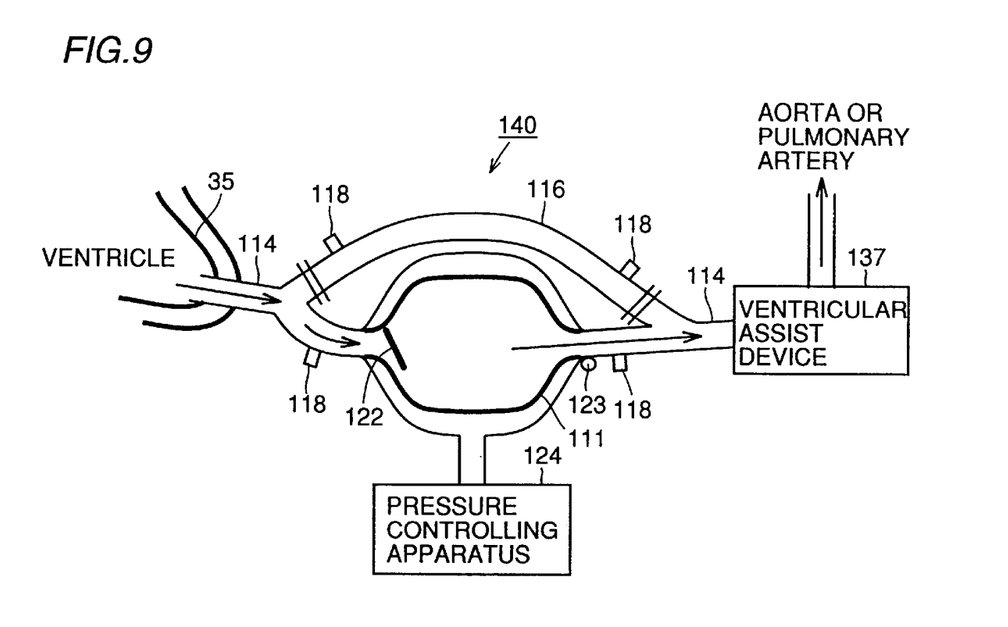
FIG. 9 represents the fourth embodiment of the present invention.
Figure 10:
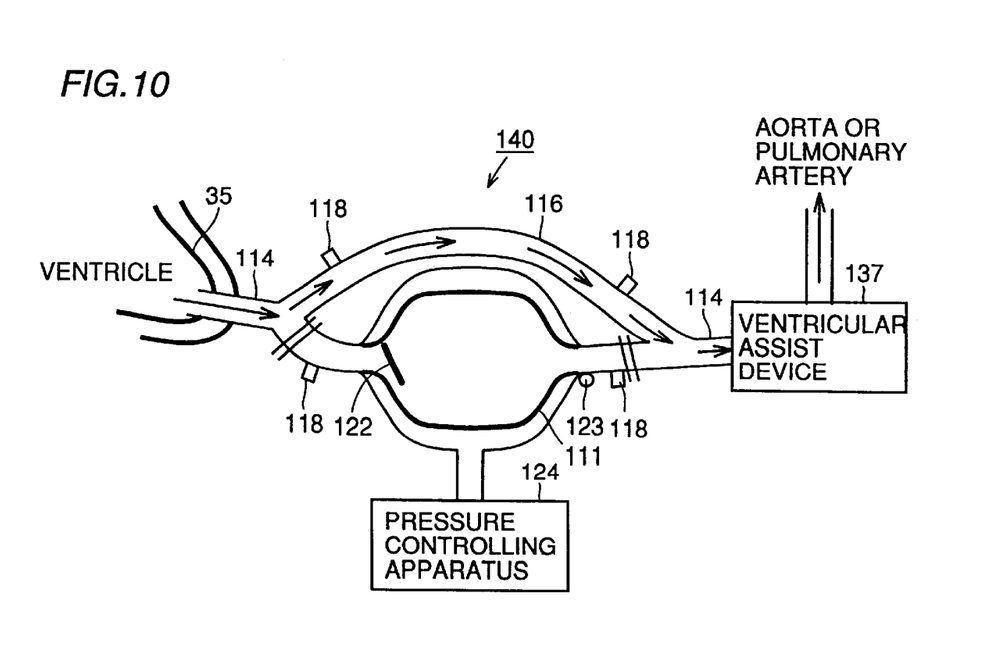
FIG. 10 represents the fourth embodiment of the present invention.

The fourth embodiment of the present invention will be described as follows. The present embodiment corresponds to the second embodiment. The present embodiment is applicable to the case of the afterload-controlling chamber 111 with the housing 121 shown in FIG. 7 and also applicable to the case of the simplified variation shown in FIG. 8. Based on the example shown in FIG. 7, an example for the present embodiment is illustrated in FIGS. 9 and 10. FIGS. 9 and 10 show a particular example of an auxiliary apparatus 140 for a ventricular assist device in accordance with the fourth embodiment. In the fourth embodiment, as shown in FIGS. 9 and 10, a bypass conduit 116 is provided parallel to the auxiliary apparatus 110 in the third embodiment. Except for this point, the present embodiment is basically the same as the third embodiment. The bypass conduit 116 is made from the same anti-thrombogenic material as that of the blood conduit 114 in the auxiliary apparatus 110 for the ventricular assist device in accordance with the third embodiment. When effective cardiac contractions are observed, the bypass conduit 116 is closed, and the route through the afterload-controlling chamber 111 is opened (FIG. 9). In this case, the apparatus is functionally equivalent to the auxiliary apparatus 110 of the third embodiment.

When there is no effective cardiac contraction, the route through the afterload-controlling chamber 111 is closed, and the bypass conduit 116 is opened (FIG. 10). In this case, the present embodiment is functionally equivalent to the case, in which the conventional ventricular assist device 137 is only used. Namely, like the conventional ventricular assist device 137, the blood in the ventricle 35 is sucked by the ventricular assist device 137 and pumped into the aorta (when the left heart is assisted) or into the pulmonary artery (when the right heart is assisted).

It is clearly understood that the embodiments described above are by way of illustration and example only and are not to be taken by way of limitation. The scope of the present invention is limited only by the terms of the appended claims, and covers all the modifications within the scope of the claims and the equivalents thereof.

What is claimed is:

1. A ventricular assist device to be provided between a ventricle of a native heart and an artery, comprising:
    a first blood conduit carrying blood from said ventricle to said ventricular assist device;
    a one-way valve, which is provided in said blood conduit and can open only toward said ventricular assist device;
    an afterload-controlling chamber temporarily storing the blood ejected from said ventricle;
    a blood pump providing blood temporarily stored in said afterload-controlling chamber for the artery; and
    pressure maintaining means for maintaining pressure in said afterload-controlling chamber within a predetermined range.

2. The ventricular assist device as defined in claim 1, wherein said predetermined range of pressure during ventricular systole is a pressure range that is lower than arterial pressure, and said predetermined range during ventricular diastole is a pressure range that keeps said one-way valve closed.

3. The ventricular assist device as defined in claim 2, further comprising pressure adjusting means for maintaining the pressure of said afterload-controlling chamber within a predetermined range.

4. The ventricular assist device as defined in claim 2, further comprising a flowmeter measuring flow rates of blood pumped into said artery by said blood pump.

5. The ventricular assist device as defined in claim 4, further comprising means for controlling the flow rate of said blood pump on the basis of the flow rate measured with said flowmeter.

6. The ventricular assist device as defined in claim 5, wherein said control means controls flow rate of said blood pump additionally on the basis of the pressure measured by said pressure-measuring means.

7. The ventricular assist device as defined in claim 1, further comprising:
    pressure-measuring means for measuring the pressure of said afterload-controlling chamber, wherein said blood pump includes means for controlling the flow rate of said blood pump on the basis of said pressure measured by said pressure-measuring means.

8. The ventricular assist device as defined in the claim 1, further comprising:

a second blood conduit that connects said afterload-controlling chamber with said blood pump; and a bypass conduit that connects a portion proximal to said one-way valve in said first blood conduit with said second blood conduit, and is parallel to a normal route consisting of said first and second blood conduits with said afterload-controlling chamber in between.

9. The ventricular assist device as defined in claim 8, further comprising means for closing either said bypass conduit or said normal conduits.

10. The ventricular assist device as defined in claim 9, wherein said bypass conduit and said normal conduits are provided with ports for administration of medicine.

11. A method of controlling a ventricular assist device, which is provided between a ventricle of a native heart and an artery, and consists of a first blood conduit carrying blood from said ventricle to said ventricular assist device, a one-way valve that is provided in said first blood conduit and can open only toward said ventricular assist device, an afterload-controlling chamber that temporarily stores the blood ejected from said ventricle, and a blood pump that pumps blood in said afterload-controlling chamber into the artery, comprising the step of:

maintaining the pressure of said afterload-controlling chamber within a predetermined range that is lower than arterial pressure during ventricular systole, and within such a predetermined range that said one-way valve is kept closed during ventricular diastole.

12. The method of controlling a ventricular assist device as defined in claim 11, wherein said step of maintaining the pressure within said predetermined range includes the steps of:

measuring pressure of said afterload-controlling chamber; and adjusting the flow rate of said blood pump so that said measured pressure is kept within said predetermined range.

13. The method of controlling a ventricular assist device as defined in claim 11, further comprising the steps of:

preparing a bypass conduit from said first blood conduit to said blood pump, in parallel to a normal route through said afterload-controlling chamber; and feeding blood to the artery through said bypass conduit when effective contraction of said heart is not observed, and feeding blood to the artery through said normal route when effective contraction of said heart is observed.

14. An auxiliary apparatus for a ventricular assist device, which is to be provided between a ventricle of a native heart and a ventricular assist device, comprising:

a first blood conduit carrying the blood ejected from said ventricle to said ventricular assist device;

a one-way valve, which is provided in said first blood conduit and can open only toward said ventricular assist device;

an afterload-controlling chamber, which temporarily stores the blood ejected from said ventricle; and pressure-maintaining means for maintaining pressure of said afterload-controlling chamber within a predetermined range that is lower than arterial pressure during ventricular systole, and within such a predetermined range that said one-way valve is kept closed during ventricular diastole.

15. The auxiliary apparatus as defined in claim 14, further comprising pressure adjusting means for maintaining said afterload-controlling chamber at a predetermined pressure.

16. The auxiliary apparatus as defined in claim 14, further comprising a flowmeter measuring flow rates from said ventricular assist device to said artery.

17. The auxiliary apparatus as defined in claim 14, further comprising:

a second blood conduit that connects said afterload-controlling chamber with said ventricular assist device; and a bypass conduit that connects a portion proximal to said one-way valve in said first blood conduit with said second blood conduit, and is parallel to a normal route consisting of said first and second blood conduits with said afterload-controlling chamber in between.

18. The auxiliary apparatus as defined in claim 17, further comprising means for closing either said bypass conduit or said normal conduits.

19. The auxiliary apparatus as defined in claim 18, wherein said bypass conduit and said normal conduits are provided with ports for administration of medicine.

* * * * *